United States Patent [19]
Bacehowski et al.

[11] Patent Number: 5,858,016
[45] Date of Patent: Jan. 12, 1999

[54] STERILE/ASEPTIC CONNECTOR

[75] Inventors: David Bacehowski, Wildwood, Ill.; David Cerny, Lilburn, Ga.; Dean Glash, McHenry, Ill.; Richard Afflerbaugh, Libertyville, Ill.; Joseph West, Jr., LakeVilla, Ill.

[73] Assignee: Baxter International Inc., Deerfield, Ill.

[21] Appl. No.: 914,169

[22] Filed: Jul. 14, 1992

[51] Int. Cl.⁶ ............................................. A61B 19/00
[52] U.S. Cl. ......................... 604/408; 604/410; 604/49; 604/56
[58] Field of Search ................... 604/403, 408, 604/410, 415, 416; 156/250, 251, 261, 289; 427/384, 333; 138/103

[56] References Cited

U.S. PATENT DOCUMENTS

| | | |
|---|---|---|
| Re. 32,056 | 12/1985 | Granzow et al. . |
| 2,622,598 | 12/1952 | Rosenblum .......................... 604/403 |
| 4,022,256 | 5/1977 | Berkman et al. . |
| 4,157,723 | 6/1979 | Granzow et al. . |
| 4,253,500 | 3/1981 | Williams . |
| 4,274,453 | 6/1981 | Lee . |
| 4,325,417 | 4/1982 | Boggs et al. . |
| 4,369,779 | 1/1983 | Spencer . |
| 4,434,822 | 3/1984 | Bellamy et al. . |
| 4,507,119 | 3/1985 | Spencer . |
| 4,521,263 | 6/1985 | Benin et al. . |
| 4,610,670 | 9/1986 | Spencer . |
| 4,619,642 | 10/1986 | Spencer . |
| 4,753,697 | 6/1988 | Shaposka et al. . |
| 4,770,735 | 9/1988 | Shaposka et al. . |
| 4,793,880 | 12/1988 | Shaposka et al. . |
| 4,807,675 | 2/1989 | Sharp . |
| 4,869,909 | 9/1989 | Takahashi et al. .................. 427/384 X |
| 4,992,312 | 2/1991 | Frisch ................. 427/333 X |
| 5,070,597 | 12/1991 | Holt et al. ........................ 138/103 X |

*Primary Examiner*—Robert A. Hafer
*Assistant Examiner*—Benjamin K. Koo
*Attorney, Agent, or Firm*—Robert M. Barrett; Amy L. H. Rockwell; Bradford R. L. Price

[57] ABSTRACT

An aseptic/sterile fluid connection between two containers is formed by radio frequency sealing together portions of transfer regions of two containers. Each transfer region has a layer of a relatively high melt temperature material such as a rubber or elastomer positioned between two outer container walls made of a flexible thermoplastic, for example polyvinyl chloride. The transfer regions are placed in registry, and the radio frequency welding fuses together portions of adjacent container outer walls and forms a fluid opening therethrough.

22 Claims, 3 Drawing Sheets

STERILE/ASEPTIC CONNECTOR

BACKGROUND OF THE INVENTION

The present invention relates generally to a method and means for providing sterile/aseptic transfer of fluids between two containers. More particularly, the present invention relates to the formation of a sterile/aseptic connection between two containers.

As described in U.S. Pat. No. 4,022,256, the problem of the sterile transfer of fluid arises in a number of different areas. One area in particular includes the area of blood handling. Since blood contains several major different components, each serving a unique function, the use of whole blood for transfusion has become unnecessary in many cases. Instead, required components can be removed, allowing the balance of the blood to be employed elsewhere. Thus, blood component therapy has helped to ease the blood storage shortage somewhat, at a time of rapidly increasing demand.

In U.S. Pat. No. 4,022,256, the disclosure of which is incorporated herein by reference, there is described an arrangement wherein two sterile containers, one of which has a fluid which is desired to transfer to the other, are each formed of a plastic tube, or have a tube coupled thereto as an extension from the interior of the respective containers. Each tube has near a closed end or somewhere along its length, a "sterile transfer region" comprising a plastic material ("Material One") which can be made to melt and flow at a sterilizing temperature. These sterile transfer regions which can have any desired closed cross-sectional area, also contain a liner or window of a second material ("Material Two") on an inside thereof. Material Two will not melt at the temperature at which Material One melts and flows.

The containers are positioned so that their sterile transfer regions, overlap and are pressed against one another in a manner so that where they are in contact, there is an interface region of the meltable material, Material One, while the inside liners, constructed from Material Two, internally cover the walls opposite the location where the walls of the two sterile transfer regions touch. The region where the two sterile transfer regions touch is clamped together between two opposing jaws of a conduction heating device wherein one jaw may be a flat surface.

The disclosed connection system requires the use of exotic and relatively costly materials such as fluorinated ethylene propylene copolymer as the liner material. Moreover, the particular means used for melting the layers constructed from Material One can be cumbersome and ill-suited for some materials.

Another connection system is disclosed in U.S. Pat. No. 4,157,723. In this patent, there is disclosed a connection which may be formed between two sealed conduits in which each conduit carries an opaque, thermoplastic wall portion preferably having a melting range above essentially 200° C. Preferably, the opaque thermoplastic wall portions are carried on the conduit about their periphery by transparent wall portions of the conduit. The opaque wall portions of the conduits are brought together into facing contact, and then exposed to sufficient radiant energy to cause the opaque wall portions to fuse together, and to open an aperture through the fused wall portions. This provides a sealed communication between the interiors of the conduits. The patent states that alternatively RF energy can be utilized.

In U.S. Pat. No. 4,325,417, there is disclosed another connector member for sealed conduits utilizing a crystalline plastic barrier membrane. In this patent, there is disclosed a connector member for a fluid flow path which comprises a transparent housing enclosing an opaque barrier membrane or wall portion blocking flow through the flow path. The barrier membrane is adapted to be openable by exposure to radiant energy from the interior through the transparent housing. In accordance with the disclosure, the barrier membrane is made of a predominantly crystalline plastic material, and accordingly, exhibits a relatively sharp melting point for improved opening characteristics upon exposure to the radiant energy.

In U.S. Pat. No. 4,434,822, there is disclosed a system for the sterile mixing of materials. In this patent, there is disclosed a fluid transfer assembly including first and second connector members, each associated with a fluid conduit and having a meltable wall which normally seals the connector member, and thus the associated conduit. The connector members can be coupled together with the meltable walls positioned in facing contact. One of the meltable walls includes a radiant energy absorbing material. The other meltable wall is relatively non-absorbent radiant energy, but does conduct heat energy. By exposing the coupled assembly to a source of radiant energy, the one wall melts in response to thermal radiation, while the other wall conducts heat energy from the melting wall to also melt. By melting, the walls open a fluid path between the fluid conduits.

Yet another sterile connector is disclosed in U.S. Pat. No. 4,253,500. In this patent, there is disclosed a sterile connector adapted for multiple junctions wherein a sealed, sterile connection may be provided between a pair or more of containers having transparent, flexible, thermoplastic sealed walls, each of which contains an opaque, relatively rigid, hollow sealing member in the general shape of a truncated cone, open at both ends. The containers are brought together in facing contact, and the hollow sealing members are nested together with portions of the transparent walls of the containers positioned therebetween. The nested, sealing member cones are irradiated with infrared energy through the transparent container walls to heat the nested sealing members. As a result of this, heat is conducted to the portions of the transparent walls between the nested sealing members to seal the portions of the transparent walls together in an annular area between the sealing members. A portion of the transparent walls retained in the nested sealing members may be torn away to make a sterile connection between the two containers.

SUMMARY OF THE INVENTION

The present invention provides an improved method and means for providing sterile/aseptic transfer of fluids between two containers. To this end, the present invention provides a sterile/aseptic connector utilizing radio frequency to permanently seal or join together two containers each having a transfer region with flexible thermoplastic outer walls, e.g. polyvinyl chloride (PVC), including an inner liner area of a high melt temperature, bio-compatible low dielectric material such as, a rubber or elastomer, for example silicone rubber.

In an embodiment, the invention provides a flexible container with polyvinyl chloride outer walls and a high melt temperature, low dielectric deformable elastomer or rubber inner liner.

In an embodiment, the invention provides a sterile fluid connection between two sterile containers comprising two adjacent layers of a thermoplastic fused together in part and including an opening formed in the fused portion.

In an embodiment, the invention provides a sterile/aseptic connection system including a radio frequency energy source and sealing dies capable of applying pressure while delivering sealing energy to effectively seal two such flexible containers together.

In an embodiment, the invention provides a method for forming a sterile/aseptic connection between two containers where each container is provided with a transfer region, each transfer region is provided with a high melt temperature rubber or elastomer layer sandwiched between two layers of PVC, the two transfer regions are placed in registry, and then radio frequency welding energy is applied to melt together two adjacent PVC layers and to create a fluid opening therethrough.

An advantage of the invention is the use of a low dielectric, high melt temperature inner liner layer in the form of a common rubber or elastomer as opposed to an exotic costly laminated matrix of fluorinated ethylene propylene copolymer.

An additional advantage provided by the invention is that the fabrication of a disposable component is made less costly because the inner liner material can simply be placed within an existing container design during manufacture.

Yet a further advantage provided by the invention is that polyvinyl chloride materials are more responsive to radio frequency energy than induction heat sealing such that energy can be focused at the interface between the two containers to be joined to create a more effective and reliable weld or seal.

And yet a further advantage of the invention is that having a flexible, deformable high melt temperature material as the inner layer allows the welded junction to more readily and reproducibly conform to the shape of the sealing die.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

As described above, the invention provides a method and means for creating an aseptic or sterile connection between two containers. Thus, the invention includes not only the structure of the connection but also the method by means of which it is formed.

Unless otherwise qualified, "container" and "enclosure" as used herein and in the claims refers both to enclosures and containers such as bags and the like as well as tubes and the like. Additionally, unless otherwise qualified, "liner" or "patch" as used in the Detailed Description or the claims, refers to a film or layer of material of any surface area, i.e., "patch" is not meant to limit the size of a layer or region to a relatively small area and likewise, "liner" does not necessarily mean a large area.

Figure 1:
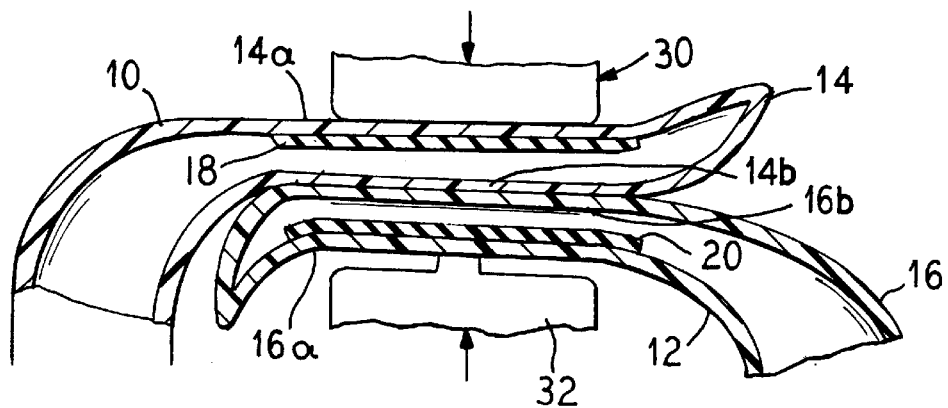
FIG. 1 illustrates, in cross-sectional view, the positioning of two flexible containers, constructed pursuant to the present invention, between a pair of sealing dies of a radio frequency heating device for sealing the container together.

As illustrated in FIG. 1, two containers 10 and 12 can be joined together by means of an aseptic or sterile connection by fusing together portions thereof referred to herein as "transfer regions." In this regard, the containers 10 and 12 illustrated in FIG. 1 include outer walls 14 and 16, respectively, made of a thermoplastic material capable of being radio frequency sealed at, preferably, sterilizing temperatures. Such a material is, for example, polyvinyl chloride (PVC).

Pursuant to the present invention, containers 10 and 12 also include inner liner patches or portions 18 and 20, respectively, comprising a high melt temperature, low dielectric material, for example silicone rubber. This high melt temperature dielectric material melts at a temperature that is greater than the melting temperature of the outer wall material.

The shape of container 10 is such that the walls 14$a$ and 14$b$ define a cavity 22 within which a fluid can be contained. Similarly, the walls 16$a$ and 16$b$ define a cavity 24 within which a fluid can be contained. The liners 18 and 20 can be appropriately secured to the inner surfaces of the walls 14$a$ and 16$a$, respectively, for example, by melt bonding of the outer walls to the liners. It can be appreciated that by virtue of such positioning, the liners are disposed between two layers of the thermoplastic material.

However, the liners 18 and 20 need not be attached to the outer walls. It is only important to have such a liner present during formation of the aseptic/sterile connection, and thus the liner can be unattached and loosely fitted between two outer walls of a container.

Moreover, to the extent the liner is attached to the outer wall, such attachment can occur at any time prior to the time when the containers are positioned for sterile connection. Indeed, if desired, the liner can be attached to the wall at the time of compression between the two sealing dies 30 and 32.

Figure 2:
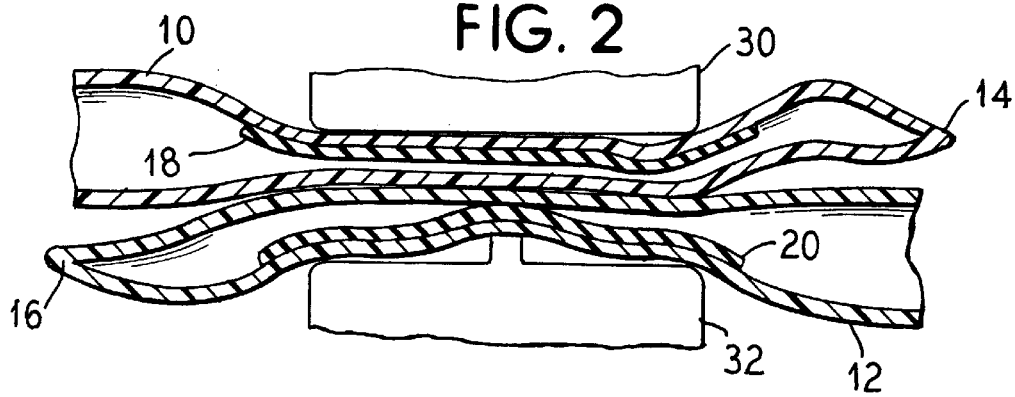
FIG. 2 illustrates clamping together of the containers between the two opposed sealing dies of the heating device of FIG. 1.

As further illustrated in FIG. 1, the transfer regions of the two containers 10 and 12 are positioned such that they are sufficiently in registry, and the container walls 14$b$ and 16$b$, not including the inner liner patches 20, lie against each other, i.e., the liner patches 18 and 20 face each other. Then, as illustrated in FIG. 2, the transfer regions are pressed together or clamped together between two opposing die members 30 and 32 of a radio frequency heating device.

Figure 3:
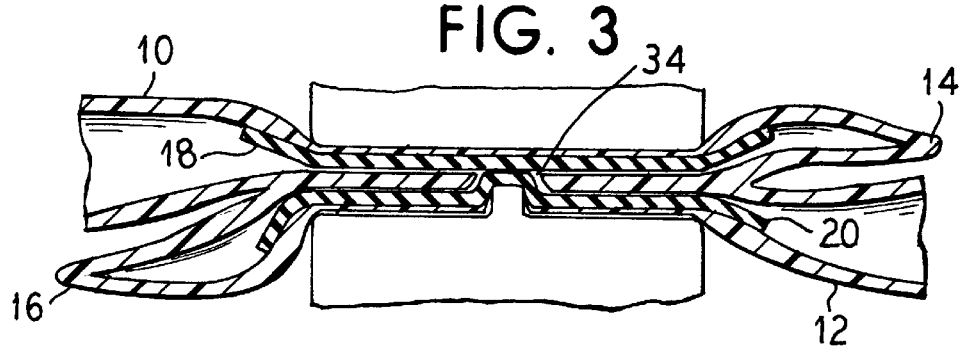
FIG. 3 illustrates application of pressure and energy such that meltable outer materials of the flexible containers of FIG. 1 become fluid at the material interface.

As illustrated in FIG. 3, pressure and energy is applied such that the meltable outer walls 14$b$ and 16$b$ become fluid at the material interface 34 between the two containers 10 and 12 and are displaced by being squeezed between the pressurized die members, while the high melt temperature liner material patches 18 and 20 do not flow. As discussed above, because the outer walls are constructed from an RF responsive material such as polyvinyl chloride, energy will be focused at the interface 34 between the two containers 10 and 12 to be joined, and, therefore, the interface walls 14b and 16b will melt before the outer walls 14a and 16a will melt.

Moreover, due to the use of radio frequency welding, it is possible to easily melt together the adjacent outer walls 14b and 16b even when a liquid is located in the containers 10 and 12. This is due to the fact that the energy is transmitted and focused on the interface area.

It can be appreciated that the inner liner layers 18 and 20 help maintain the sterility of the connection by preventing the formation of openings in the outer walls 14a and 16a opposite the interfacing walls 14b and 16b. Because these outer walls 14a and 16a do not form part of the interface and are maintained separate therefrom by the liners 18 and 20, these outer walls 14a and 16a are not subject to the concentration of radio frequency energy presented at the interface, and thus do not melt as readily.

Figure 4:
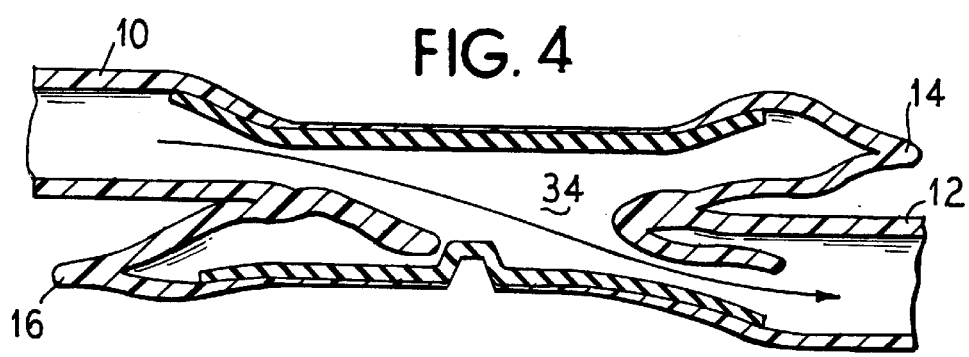
FIG. 4 illustrates a resulting aseptic/sterile fluid pathway created between the two flexible containers of FIG. 1.

As illustrated in FIG. 4, eventually, the interfacing walls 14b and 16b of the two containers 10 and 12 will melt. After a sufficient heating and squeezing time, an opening or aperture is formed in the fused area due to the squeezing action of the dies 30 and 32. Upon retraction of the die members 30 and 32 or termination of the RF energy, the materials will cool and fuse together and an aseptic/sterile pathway 34 is created between the two containers 10 and 12. The integrity of the lined walls 14a and 16a of the containers 10 and 12 is maintained by means of the inner liners 18 and 20, even though some thinning of the walls 14a and 16a can occur.

Although one liner material suitable for constructing the liners 18 and 20 is silicone rubber, other materials such as rubbers or elastomers which do not melt at sterilizing temperatures can be used as well. Silicone rubber presents a low cost acceptable material.

Additionally, materials other than PVC can be used as the outer walls 14 and 16. An important feature, however, is RF responsiveness and preferably meltability at sterilizing temperatures. By utilizing materials that melt at sterilizing temperatures, a connection can be made using temperatures that sterilize the connection site, ensuring the sterility of the process.

Figure 5:
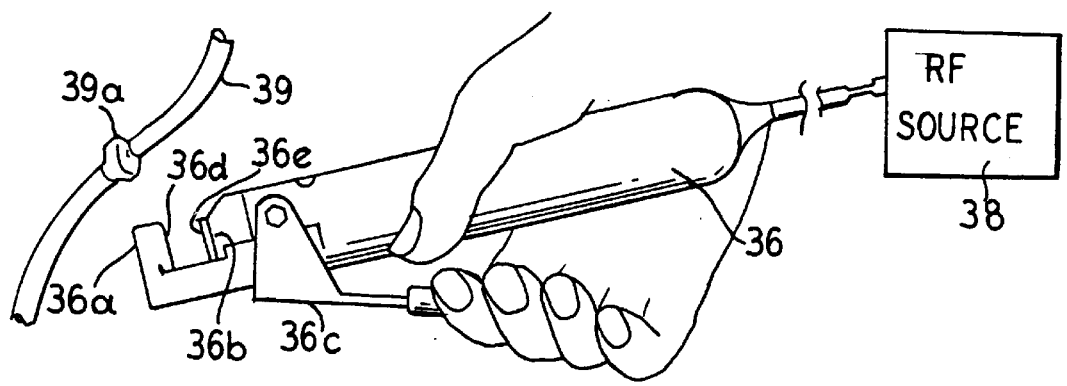
FIG. 5 illustrates in perspective view, an embodiment of a hand-held radio frequency sealing device.

One means for providing the radio frequency sealing is through the use of a modified Model 1100 laboratory handheld tube sealer provided by Engineering and Research Associates, Inc., which is illustrated in FIG. 5. The Model 1100 hand-held tube sealer is designed to seal blood bags and other heavier blood processing tubing by high frequency dielectric heating and includes the following features:

1. Sealing can be accomplished in any location reachable by hand;
2. Sealing can be achieved in approximately one second;
3. The sealer's external power control allows the operator to optimize seal time and the quality to match various types of tubing;
4. Repetitive sealing for tube segmentation can be accomplished rapidly;
5. Sealed segments can be readily separated by pulling and twisting from both sides;
6. Continuous sealing will not cause excessive heat build-up and therefore burn throughs generally will not occur; and
7. Sealing jaws, dies and lever can be easily disassembled for cleaning.

As illustrated in FIG. 5, the Model 1100 tube sealer includes a hand-held unit 36 having opposing sealing jaws 36a and 36b. Jaw 36a is movable toward and away from jaw 36b by means of a lever 36c.

The jaws 36a, 36b include sealing dies 36d and 36e, respectively, which are coupled to a radio frequency source 38 so that the dies 36a, 36e can weld together two sheets of meltable material. In FIG. 5, a tube 39 is illustrated as having been sealed closed at 39a by means of the Model 1100 tube sealer.

Figure 6:
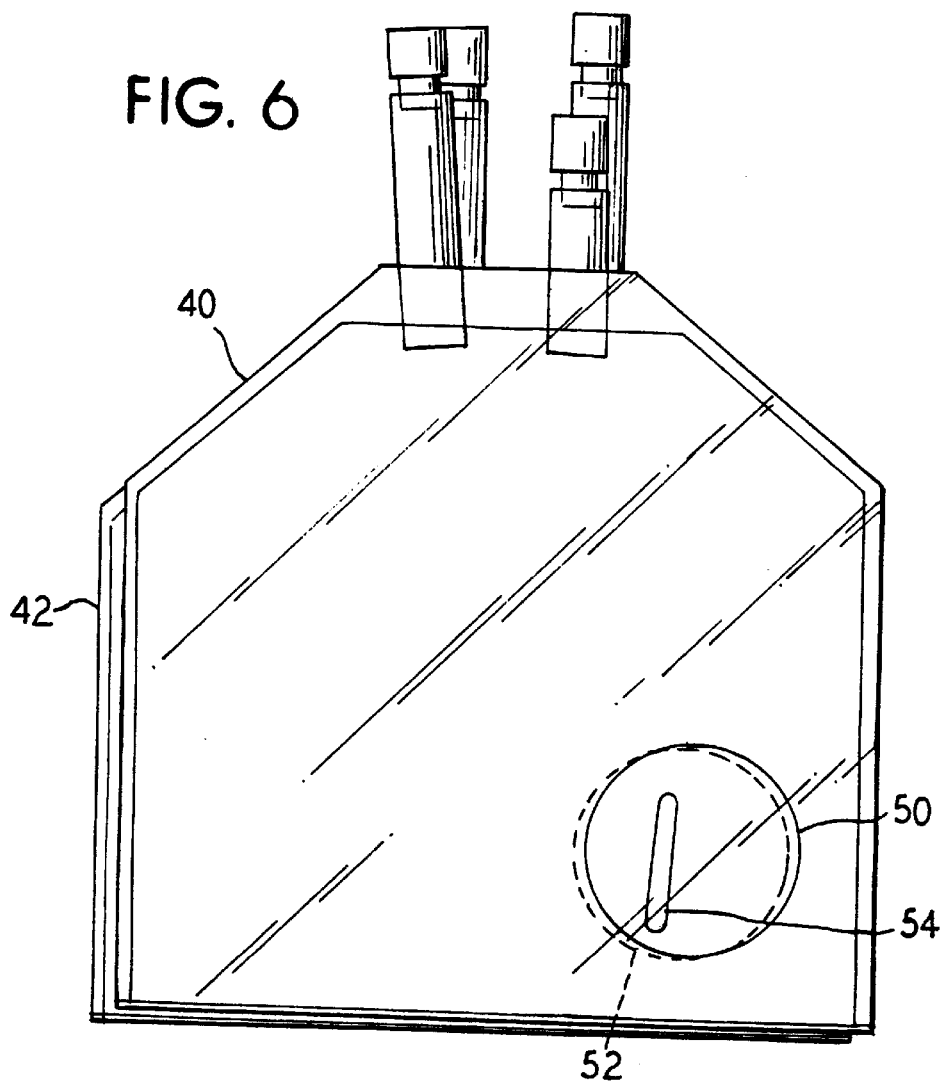
FIG. 6 illustrates a pair of containers coupled together in fluid communication by means of a connection formed according to the steps illustrated in FIGS. 1–4.

As illustrated in FIG. 6, the present invention is particularly useful in one embodiment for sealing together two blood bags 40 and 42. In this regard, as illustrated, the two blood bags 40 and 42 include suitable, flexible outer walls 44 and 46, respectively, made of, for example, polyvinyl chloride. In one corner of each of the bags 40 and 42, there is included a circular window or patch 50 or 52, respectively, of an inner liner material secured to the inner surface of one of the walls of the bags.

The bags 40 and 42 can then be positioned such that the patches overlap but face each other as described above in connection with FIG. 1. Then, by utilizing a modified device such as a modified hand-held tube sealer, a sterile/aseptic connection 54 can be made in the patch area thereby to provide a sterile connection between the two blood bags 40 and 42. Of course, the particular shape of any connection will depend on the shape of the radio frequency welding die employed. In the embodiment of FIG. 5, the connection is elongated, however, it could just as well be circular or rectangular or letter shaped, e.g., "H" shaped.

Figure 7:
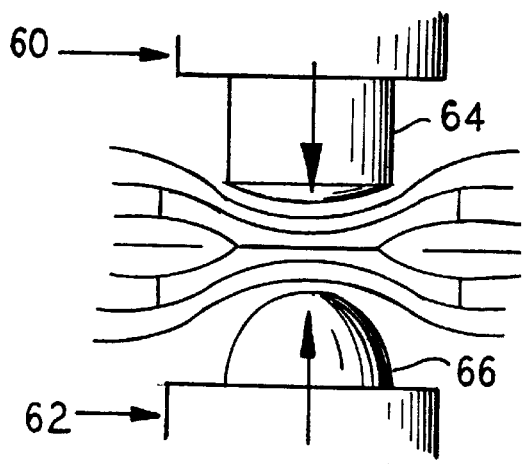
FIG. 7 illustrates in profile an embodiment of a pair of sealing dies that can be used in the method and means of FIGS. 1–4.

In FIG. 7 there is illustrated a pair of sealing dies 60 and 62 that are highly effective at concentrating radio frequency energy to melt the meltable layers at the interface area and conducting away melted matter so as to form the fluid opening in the resulting connection. It can be seen that the dies 60 and 62 include convex crowns 64 and 66 respectively. As a result, melted matter, such as the melted interfacing outer walls of flexible containers is easily pushed radially away from an axial center point of the dies, at which point an opening is formed between the two fusing interfacing outer walls. Moreover, should the container be filled with liquid, the convex shapes will push aside the liquid so that the dies will more closely press together and more fully focus the sealing energy at the interface area.

Figure 8:
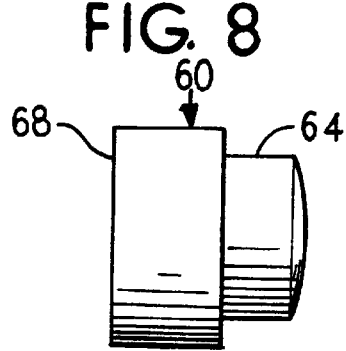
FIG. 8 illustrates an isometric view of one of the sealing dies of FIG. 7.
Figure 9:
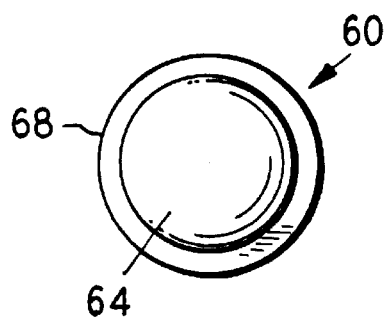
FIG. 9 illustrates an end view of the sealing die of FIG. 8.

Die 60 is illustrated in greater detail in FIGS. 8 and 9. As illustrated, the die 60 includes a cylindrical base 68. It has been found that a die 60 having a cylindrical base 68, whose diameter is 0.5 inches and whose axial length is 0.25 inches, functions satisfactorily. Concentrically disposed on an axial end of the base 68 is the crown 64 which is substantially cylindrical in shape. It has been found that a crown 64 having a diameter of 0.375 inches and an axial length of 0.187 inches functions satisfactorily.

Figure 10:
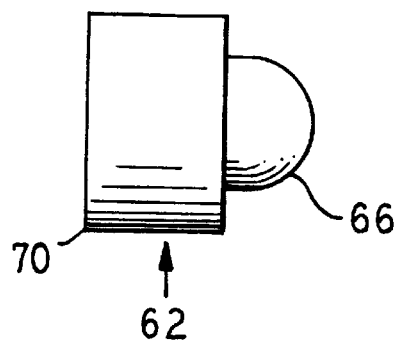
FIG. 10 illustrates an isometric view of the other sealing die of FIG. 7.
Figure 11:
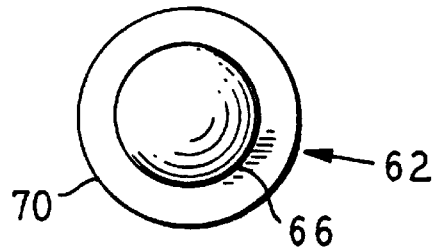
FIG. 11 illustrates an end view of the sealing die of FIG. 10.

The sealing die 62 is illustrated in greater detail in FIGS. 10 and 11. As illustrated, the die 62 includes a cylindrical base 70 on an axial end of which is disposed the somewhat hemispherically shaped crown 66.

It has been found that a die 62 having an overall axial length of 0.5 inches and its own axial length of 0.313 inches and a diameter of 0.5 inches functions satisfactorily. Likewise, it has been found that a base 70 having a crown 66 of having a diameter 0.312 inches functions satisfactorily.

While the foregoing description only describes the formation of a single connection between two containers, it should be understood that multiple connections can be made in accordance with the above method and means of the present invention.

As described above, a method and device are provided for making a sterile connection and passageway, between two separate detached containers on tubes. With respect to tubes, the tubes can extend from separate containers, or can be separately manufactured and later attached to containers. Due to the manner in which the connection is made, the interiors of the containers, or tubes, are never exposed to any possible contamination. Thus, a means for making sterile connections is provided.

It should be understood that various changes and modifications to the presently preferred embodiments described herein will be apparent to those skilled in the art. Such changes and modifications can be made without departing from the spirit and scope of the present invention and without diminishing its attendant advantages. It is, therefore, intended that such changes and modifications be covered by the appended claims.

What is claimed is:

1. A flexible sterile container comprising:

at least two RF-responsive outer walls defining a cavity therebetween made of a thermoplastic material that will melt at a first temperature; and an RF-insulative liner disposed between two RF-responsive outer walls, the liner made of a biocompatible, low dielectric material with a melting temperature above the first temperature wherein the liner is made of an elastomer.

2. The flexible sterile container of claim 1 wherein the outer walls are made of polyvinyl chloride.

3. The flexible sterile container of claim 1 wherein the liner is in the form of a disc.

4. The flexible sterile container of claim 1 wherein the liner is made of silicone rubber.

5. The flexible sterile container of claim 1 wherein the liner is secured to one of the outer walls.

6. A method of forming a sterile connection comprising the steps of:

providing two flexible containers having outer walls made of an RF-responsive thermoplastic;

providing an RF-insulative liner of a bicompatible, low dielectric material with a melting point above that of the outer walls within a transfer region of each container;

positioning the containers such that the transfer regions are, at least in part, in registry and the outer walls of the containers are adjacent;

clamping the transfer regions between dies of a radio frequency welding source;

generating a radio frequency welding signal so as to fuse together the outer walls of the containers that are adjacent to each other; and forming an opening through the fused thermoplastic walls.

7. The method of claim 6 wherein the biocompatible, low dielectric material is in the shape of a disc.

8. The method of claim 6 wherein the thermoplastic material is polyvinyl chloride.

9. A connection system for forming a sterile fluid connection between two sterile containers, comprising:

two containers having outer walls made of a thermoplastic that will melt at sterilizing temperatures and that is particularly susceptible to radio frequency welding;

a liner disposed within each container and made of a biocompatible, low dielectric material with a melting point above that of the walls of the containers;

a radio frequency source; and two welding dies associated with the radio frequency source capable of applying pressure while delivering radio frequency energy to effectively seal together portions of the outer walls of the containers when placed between the dies.

10. The connection of claim 7 wherein the low dielectric material comprises silicone rubber.

11. A method of forming a sterile connection comprising the steps of:

providing two flexible containers having outer walls made of a thermoplastic;

providing a liner of a biocompatible, low dielectric material with a melting point above that of the outer walls within a transfer region of each container wherein the bicompatible, low dielectric material is a rubber;

positioning the containers such that the transfer regions are, at least in part, in registry and outer walls of the containers are adjacent;

clamping the transfer regions between dies of a radio frequency welding source;

generating a radio frequency welding signal so as to fuse together the outer walls of the containers that are adjacent to each other; and forming an opening through the fused thermoplastic walls.

12. The method of claim 11 wherein the rubber is silicone rubber.

13. A connection system for forming a sterile fluid connection between two sterile containers, comprising:

two containers having outer walls made of a thermoplastic that will melt at sterilizing temperatures and that is particularly susceptible to radio frequency welding;

a liner disposed within each container and made of a biocompatible, low dielectric material with a melting point above that of the walls of the containers;

a radio frequency source; and two welding dies associated with the radio frequency source capable of applying pressure while delivering radio frequency energy to effectively seal together portions of the outer walls of the containers when placed between the dies wherein each die includes a crown with a convex surface at an axial end thereof.

14. A connection system for forming a sterile fluid connection between two sterile containers, comprising:

two containers having outer walls made of a thermoplastic that will melt at sterilizing temperatures and that is particularly susceptible to radio frequency welding;

a liner disposed within each container and made of a biocompatible, low dielectric material with a melting point above that of the walls of the containers;

a radio frequency source; and two welding dies associated with the radio frequency source capable of applying pressure while delivering radio frequency energy to effectively seal together portions of the outer walls of the containers when placed between the dies wherein a die has a substantially cylindrical base and a smaller substantially cylindrical crown.

15. Two blood bags coupled together in fluid communication by means of a sterile connection, the blood bags comprising outer walls of a thermoplastic material that will melt at sterilizing temperatures, each blood bag having a transfer region where a liner is disposed within the blood bag, the liner being made of a biocompatible, low-dielectric material with a melting temperature greater than that of the outer walls, the blood bags being connected at their transfer regions, the connection comprising portions of adjacent outer walls which are fused together and which include an opening therethrough wherein the liners are made of an elastomer.

16. A sterile connection comprising a plurality of layers arranged as follows:

a first thermoplastic layer;

a first liner of a low dielectric material;

second and third thermoplastic layers fused together at portions thereof and including an opening therethrough;

a second liner of a low dielectric material; and a fourth thermoplastic layer, the thermoplastic layers having a melting temperature that is lower than the melting temperature of the low dielectric material wherein the dielectric material is an elastomer.

17. The connection of claim 16 wherein the melting temperature of the thermoplastic material is at least as great as the sterilizing temperature.

18. The connection of claim 16 wherein the thermoplastic is polyvinyl chloride.

19. The connection of claim 16 wherein the first liner of a low dielectric material is secured to the first thermoplastic layer.

20. The connection of claim 19 wherein the second liner of a low dielectric material is secured to the fourth thermoplastic layer.

21. A sterile connection comprising a plurality of layers arranged as follows:

a first thermoplastic layer;

a first liner of a low dielectric material;

second and third thermoplastic layers fused together at portions thereof and including an opening therethrough;

a second liner of a low dielectric material; and a fourth thermoplastic layer, the thermoplastic layers having a melting temperature that is lower than the melting temperature of the low dielectric material wherein the low dielectric material comprises silicone rubber.

22. The system of claim 19 wherein the dies are secured within a hand-held apparatus.

* * * * *